United States Patent
Anderson et al.

(10) Patent No.: US 6,626,877 B2
(45) Date of Patent: Sep. 30, 2003

(54) MEDICAL SUCTION APPARATUS AND METHODS FOR DRAINING SAME

(75) Inventors: Barry G. Anderson, Sheboygan, WI (US); Joseph M. Hand, Sheboygan Falls, WI (US)

(73) Assignee: Bemis Manufacturing Company, Sheboygan Falls, WI (US)

( * ) Notice: Subject to any disclaimer, the term of this patent is extended or adjusted under 35 U.S.C. 154(b) by 0 days.

(21) Appl. No.: 09/819,243

(22) Filed: Mar. 28, 2001

(65) Prior Publication Data

US 2001/0037096 A1 Nov. 1, 2001

Related U.S. Application Data (60) Provisional application No. 60/192,751, filed on Mar. 28, 2000.

(51) Int. Cl.[7] ................................................. A61M 1/00
(52) U.S. Cl. ........................................ 604/319; 604/322
(58) Field of Search ........................... 604/317–326, 604/327, 332–345; 141/375

(56) References Cited

U.S. PATENT DOCUMENTS

| | | | |
|---|---|---|---|
| 1,421,325 A | 6/1922 | Walker et al. |
| 1,693,885 A | 12/1928 | Butterworth |
| 1,827,085 A | 10/1931 | Huff |
| 2,004,027 A | 6/1935 | Baxter |
| 2,009,400 A | 7/1935 | Hapgood |
| 2,073,746 A | 3/1937 | Keller |
| 2,208,028 A | 7/1940 | Harrington |
| 2,438,769 A | 3/1948 | Thomas |
| 2,641,270 A | 6/1953 | Allen |
| 2,799,301 A | 7/1957 | Ballard |
| 2,886,071 A | 5/1959 | Ramussen |
| 3,171,447 A | 3/1965 | Fowler et al. |
| 3,363,627 A | 1/1968 | Bidwell et al |
| 3,394,831 A | 7/1968 | Bathish et al. |
| 3,482,583 A | 12/1969 | Fenn |
| 3,556,101 A | 1/1971 | Economou |
| 3,603,328 A | 9/1971 | Fenn |
| 3,646,935 A | 3/1972 | Holbrooke t al. |
| 3,671,982 A | 6/1972 | Sayles |
| 3,680,560 A | 8/1972 | Pannier, Jr. et al. |
| 3,685,517 A | 8/1972 | Reynolds et al. |
| 3,699,964 A | 10/1972 | Ericson |
| 3,719,197 A | 3/1973 | Pannier, Jr. et al. |
| 3,768,478 A | 10/1973 | Fertik et al. |
| 3,780,757 A | 12/1973 | Jordan |

(List continued on next page.)

FOREIGN PATENT DOCUMENTS

| | | | |
|---|---|---|---|
| EP | 0596132 A1 | 5/1994 | ........... A61L/11/00 |
| WO | 86023430 | 4/1986 | ............. B67C/1/06 |

OTHER PUBLICATIONS

Med Inc., Medical & Environmental Design, Inc.; Promotional Product Material, Jan. 15, 1991.

*Primary Examiner*—Weilun Lo
*Assistant Examiner*—C Anderson
(74) *Attorney, Agent, or Firm*—Michael Best & Friedrich LLP (57) ABSTRACT

A method and apparatus for draining a liner-type medical suction apparatus. The method includes the acts of positioning the liner-type medical suction apparatus relative to a drainage device including a conduit, causing the conduit to communicate with the liner interior, and draining the fluid from the liner interior through the conduit. The apparatus includes a support member adapted to support the liner-type medical suction apparatus and a drainage device housing adjacent to the support member. The device also includes a conduit including a first end coupled to the drainage device housing and a second end for communication with the liner interior.

23 Claims, 5 Drawing Sheets

U.S. PATENT DOCUMENTS

| | | | |
|---|---|---|---|
| 3,782,414 A | 1/1974 | Holbrook | |
| 3,791,394 A | 2/1974 | Hammelmann | |
| 3,863,664 A | 2/1975 | Holbrook et al. | |
| 3,866,608 A | 2/1975 | Reynolds et al. | |
| 3,881,486 A * | 5/1975 | Fenton | 604/335 |
| 3,897,599 A | 8/1975 | Artzer | |
| 3,916,924 A | 11/1975 | McGowan | |
| 3,945,392 A | 3/1976 | Deaton et al. | |
| 3,958,730 A | 5/1976 | Caldwell | |
| 3,989,046 A | 11/1976 | Pannier, Jr. et al. | |
| 3,995,333 A | 12/1976 | Stephens | |
| 4,004,590 A | 1/1977 | Muriot | |
| 4,015,603 A | 4/1977 | Kurtz et al. | |
| 4,049,555 A | 9/1977 | Matherne | |
| 4,056,284 A | 11/1977 | Stoltefuss et al. | |
| 4,058,412 A | 11/1977 | Knapp et al. | |
| 4,084,723 A | 4/1978 | Parker | |
| 4,090,635 A | 5/1978 | Nelson et al. | |
| 4,108,336 A | 8/1978 | Anderson, Jr. | |
| 4,112,948 A | 9/1978 | Kurtz et al. | |
| 4,135,515 A | 1/1979 | Muriot | |
| 4,157,718 A | 6/1979 | Baehr | |
| 4,195,633 A | 4/1980 | Nehring et al. | |
| 4,195,672 A | 4/1980 | Freeman | |
| 4,228,798 A | 10/1980 | Deaton | |
| 4,238,892 A | 12/1980 | Geiss | |
| 4,245,637 A | 1/1981 | Nichols | |
| 4,258,824 A | 3/1981 | Kurtz et al. | |
| 4,275,732 A | 6/1981 | Gereg | |
| 4,306,557 A | 12/1981 | North | |
| 4,321,922 A | 3/1982 | Deaton | |
| 4,341,568 A | 7/1982 | Christensen | |
| 4,345,342 A | 8/1982 | Saito | |
| 4,356,084 A | 10/1982 | Hatton et al. | |
| 4,363,340 A | 12/1982 | Naftulin | |
| 4,384,580 A | 5/1983 | Leviton | |
| 4,388,922 A | 6/1983 | Telang | |
| 4,429,803 A | 2/1984 | Butterfield | |
| 4,430,084 A | 2/1984 | Deaton | |
| 4,430,085 A | 2/1984 | Ahrens | |
| 4,455,140 A | 6/1984 | Joslin | |
| 4,484,920 A | 11/1984 | Kaufman et al. | |
| 4,519,427 A | 5/1985 | Ono et al. | |
| 4,540,413 A | 9/1985 | Russo | |
| 4,559,664 A | 12/1985 | Bohme et al. | |
| 4,586,549 A | 5/1986 | White | |
| 4,629,159 A | 12/1986 | Wellenstam | |
| 4,631,050 A | 12/1986 | Reed et al. | |
| 4,666,063 A | 5/1987 | Holoubek et al. | |
| 4,673,006 A | 6/1987 | Speck | |
| 4,676,281 A | 6/1987 | Nord | |
| 4,676,287 A | 6/1987 | Fitzwater | |
| 4,681,571 A | 7/1987 | Nehring | |
| 4,685,480 A | 8/1987 | Eck | |
| 4,698,060 A | 10/1987 | D'Antonio et al. | |
| 4,704,106 A | 11/1987 | Shave et al. | |
| 4,715,855 A | 12/1987 | D'Antonio et al. | |
| 4,735,610 A | 4/1988 | Akkas et al. | |
| 4,740,202 A | 4/1988 | Stacey et al. | |
| 4,749,010 A | 6/1988 | Petell | |
| 4,762,241 A | 8/1988 | Lang | |
| 4,770,787 A | 9/1988 | Heath et al. | |
| 4,781,707 A | 11/1988 | Boehringer et al. | |
| 4,785,963 A | 11/1988 | Magley | |
| 4,795,428 A | 1/1989 | Hwang | |
| 4,795,448 A | 1/1989 | Stacey et al. | |
| 4,808,159 A | 2/1989 | Wilson | |
| 4,809,860 A | 3/1989 | Allen | |
| 4,813,563 A | 3/1989 | Ogden et al. | |
| 4,820,351 A | 4/1989 | Hambleton et al. | |
| 4,857,063 A | 8/1989 | Glenn | |
| 4,863,446 A | 9/1989 | Parker | |
| 4,867,738 A | 9/1989 | Mintz | |
| 4,870,975 A | 10/1989 | Cronk et al. | |
| 4,889,531 A | 12/1989 | D'Antonio et al. | |
| 4,902,284 A | 2/1990 | D'Antonio et al. | |
| 4,905,325 A | 3/1990 | Colditz | |
| 4,913,179 A | 4/1990 | Engel et al. | |
| 4,913,197 A | 4/1990 | Friedrich | |
| 4,926,915 A | 5/1990 | Deussen et al. | |
| 4,955,874 A | 9/1990 | Farrar et al. | |
| 4,957,491 A | 9/1990 | Parker | |
| 4,961,440 A | 10/1990 | Wright | |
| 4,967,814 A | 11/1990 | Day, Jr. | |
| 4,969,491 A | 11/1990 | Kiplinger | |
| 4,972,976 A | 11/1990 | Romero | |
| 5,011,470 A | 4/1991 | Kurtz et al. | |
| 5,024,613 A | 6/1991 | Vasconcellos et al. | |
| 5,026,358 A | 6/1991 | Everett, Jr. et al. | |
| 5,027,872 A | 7/1991 | Taylor et al. | |
| 5,033,492 A | 7/1991 | Mertens et al. | |
| 5,045,077 A | 9/1991 | Blake, III | |
| 5,049,273 A | 9/1991 | Knox | |
| 5,053,026 A | 10/1991 | Andersen et al. | |
| 5,064,101 A | 11/1991 | Richter et al. | |
| 5,067,950 A | 11/1991 | Broadnax, Jr. | |
| 5,071,035 A | 12/1991 | Kiplinger | |
| 5,078,677 A | 1/1992 | Gentelia et al. | |
| 5,119,830 A | 6/1992 | Davis | |
| 5,121,778 A | 6/1992 | Baker et al. | |
| 5,154,712 A | 10/1992 | Herweck et al. | |
| 5,185,007 A | 2/1993 | Middaugh et al. | |
| 5,186,195 A | 2/1993 | Wall | |
| 5,192,439 A | 3/1993 | Roth et al. | |
| 5,195,994 A | 3/1993 | Dieringer | |
| 5,217,038 A | 6/1993 | Pinder | |
| 5,222,530 A | 6/1993 | Baker et al. | |
| 5,242,434 A | 9/1993 | Terry | |
| 5,273,083 A | 12/1993 | Burrows | |
| 5,300,050 A | 4/1994 | Everett, Jr. et al. | |
| 5,349,995 A | 9/1994 | Perez | |
| 5,351,859 A | 10/1994 | Jansen | |
| 5,380,289 A | 1/1995 | Hemstreet et al. | |
| 5,380,314 A | 1/1995 | Herweck et al. | |
| 5,437,836 A | 8/1995 | Yamada | |
| 5,439,460 A * | 8/1995 | Hoover | 128/912 |
| 5,460,193 A | 10/1995 | Levallois et al. | |
| 5,470,324 A | 11/1995 | Cook et al. | |
| 5,546,979 A | 8/1996 | Clark, II et al. | |
| 5,599,331 A | 2/1997 | Hemstreet et al. | |
| 5,620,428 A | 4/1997 | Hand | |
| 5,624,417 A | 4/1997 | Cook et al. | |
| 5,637,103 A | 6/1997 | Kerwin et al. | |
| 5,669,892 A | 9/1997 | Keogh et al. | |
| 5,678,564 A | 10/1997 | Lawrence et al. | |
| 5,683,371 A | 11/1997 | Hand | |
| 5,688,255 A | 11/1997 | Hand | |
| 5,725,516 A | 3/1998 | Cook et al. | |
| 5,741,237 A | 4/1998 | Walker | |
| 5,776,118 A | 7/1998 | Seifert et al. | |
| 5,776,260 A | 7/1998 | Dunn et al. | |
| 5,807,359 A | 9/1998 | Bemis et al. | |
| 5,837,103 A | 11/1998 | Trokhan et al. | |
| 5,871,476 A | 2/1999 | Hand | |
| 5,901,717 A | 5/1999 | Dunn et al. | |
| 5,931,822 A * | 8/1999 | Bemis et al. | 604/317 |
| 6,027,490 A | 2/2000 | Radford et al. | |
| 6,152,902 A * | 11/2000 | Christian et al. | 604/320 |
| 6,244,311 B1 | 6/2001 | Hand et al. | |
| 6,358,232 B1 | 3/2002 | Hand et al. | |
| 6,368,310 B1 | 4/2002 | Bemis et al. | |

\* cited by examiner

MEDICAL SUCTION APPARATUS AND METHODS FOR DRAINING SAME

RELATED APPLICATIONS

Priority is claimed under 35 U.S.C. §119 to U.S. patent application No. 60/192,751, filed Mar. 28, 2000.

BACKGROUND OF THE INVENTION

The invention relates to draining bodily fluid contained in the liner of a liner-type medical suction apparatus.

Medical suction systems are used in hospital environments and particularly during various surgical procedures to drain and store bodily fluid from a patient. In general, medical suction systems are used in conjunction with a vacuum source which enables the bodily fluid to be drained from the patient.

One type of medical suction system used to drain and contain fluid from a patient is an apparatus including a disposable bag-like liner and a cover secured to the liner. Such liners are thin-walled pliable plastic members. The cover typically includes a patient port for receiving the fluid from a patient and a vacuum port for establishing a vacuum within the liner. The vacuum draws fluid from the patient through the patient port for collection in the liner.

It has become important in environments such as hospitals to eliminate the handling of and thus reduce personnel exposure to bodily fluids. Hospitals typically dispose of the bodily fluid contained in a liner-type medical suction apparatus in various ways. Bodily fluid can be poured from the liner through a port in the cover down the hospital sink and into the sewer system, can be incinerated as a liquid or solid, or can be disposed of at an approved hazardous waste site. Since the liner is in the form of a pliable bag filled with liquid, special disposal handling is required in order to prevent puncturing or bursting due to contact with sharp objects.

SUMMARY OF THE INVENTION

The invention provides improved methods and apparatus for removing body fluids from a liner-type medical suction apparatus to eliminate the potential for a person handling the apparatus to come into contact with the fluid being drained.

Specifically, the invention provides for methods of draining bodily fluid from a liner that is drained of potentially hazardous fluid without contact with the fluid. The liner is drained in conjunction with a drainage device. Various types of drainage devices can be employed to drain the liner.

More particularly, the invention provides a method for draining a liner-type medical suction apparatus, the liner-type medical suction apparatus including a liner, a liner interior filled with fluid, a cover, and a port in the cover. The method includes providing a drainage device, the drainage device including a conduit and a cradle. The method also includes positioning the cover of the liner-type medical suction apparatus within the cradle of the drainage device with the liner-type suction apparatus inverted, causing the conduit to communicate with the liner interior through the port, and draining the fluid from the liner interior through the conduit.

The invention also provides another method for draining a liner-type medical suction apparatus, the liner-type medical suction apparatus including a liner, a liner interior filled with fluid, a cover, and a port in the cover. The method includes providing a drainage device, the drainage device including a movable support member and a conduit. The method also includes positioning the liner-type medical suction apparatus in a substantially upright position within the support member, attaching the conduit to the port, and moving the support member to cause the liner-type medical suction apparatus to move from the substantially upright position to a position in which the fluid flows out of the liner interior into the conduit.

The invention also provides a medical apparatus including a liner-type medical suction apparatus. The liner-type medical suction apparatus includes a liner, a liner interior for containing fluid, a cover, a port in the cover, and a pre-attached tube coupled to the port and extending into the liner interior. The medical apparatus includes a drainage device including a housing. The medical apparatus also includes a conduit including a first end coupled to the drainage device housing and a second end coupleable to the port so that fluid in the liner interior can flow through the pre-attached tube and the conduit to the drainage device.

The invention also provides another device for draining a liner-type medical suction apparatus, the liner-type medical suction apparatus including a liner, a liner interior filled with fluid, a cover, and a port in the cover. The device includes a drainage device housing and a cradle coupled to the drainage device housing, the cradle being adapted to support the cover of the liner-type medical suction apparatus when the liner-type medical suction apparatus is in an inverted position. The device also includes a breakout pipe including a first end coupled to the cradle and a second end for communication with the liner interior. The breakout pipe is movable upwardly between a storage position in which the second end is stored substantially within the cradle and a drainage position in which the second end is in communication with the liner interior through the cover.

The invention also provides still another device for draining a liner-type medical suction apparatus, the liner-type medical suction apparatus including a liner, a liner interior, a cover, and a port in the cover. The device includes a drainage device housing, a drain coupled to the drainage device housing, and a conduit including a first end coupled to the drain and a second end adapted for attachment to the port. The device also includes a support member coupled to the drainage device housing and adapted to support the liner-type medical suction apparatus. The support member is movable between a loading position in which the liner-type medical suction apparatus is in a substantially upright position and a drainage position in which the liner-type medical suction apparatus is in a position in which the fluid flows through the conduit to the drain.

Other features and advantages of the invention will become apparent to those of ordinary skill in the art upon review of the following description, claims and drawings.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

Figure 1:
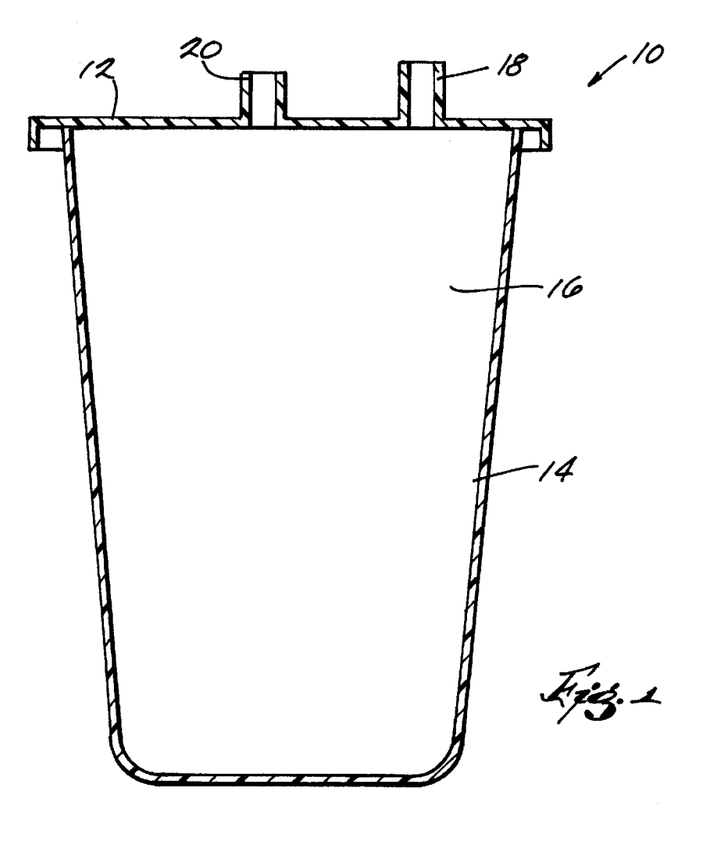
FIG. 1 is a front view of a liner-type medical suction apparatus.

With reference to FIG. 1, there is shown a liner-type medical suction apparatus 10. The apparatus 10 includes a cover 12 and a liner 14 suitably attached to the cover 12. The liner 14 is a thin-walled bag having an interior 16 adapted to hold the fluid drained from a patient. The liner 14 is preferably fabricated from a plastic such as ultra low density polyethylene, however, other materials can be used as desired.

The cover 12 includes a patient port 18, a suction port 20, and other access ports as desired. A patient conduit is connectable to the patient port 18 to enable communication between the patient and the interior 16 of the liner 14. A suction conduit is connectable to the suction port 20 to enable communication between the interior 16 of the liner 14 and a suction source, such as a hospital suction system.

To drain fluid from a patient, the patient and suction conduits are respectively secured to the patient and suction ports 18 and 20. The liner 14 is supported by a stand or by a rigid outer container or canister (not shown), and fluid is drained from a patient as is conventionally known.

When it is desired to drain the fluid contained in the liner 14, one of the seven methods described herein can be employed to drain the fluid contents from the interior 16 of the liner 14 while eliminating any contact with the fluid by the person handling the apparatus 10.

Figure 2:
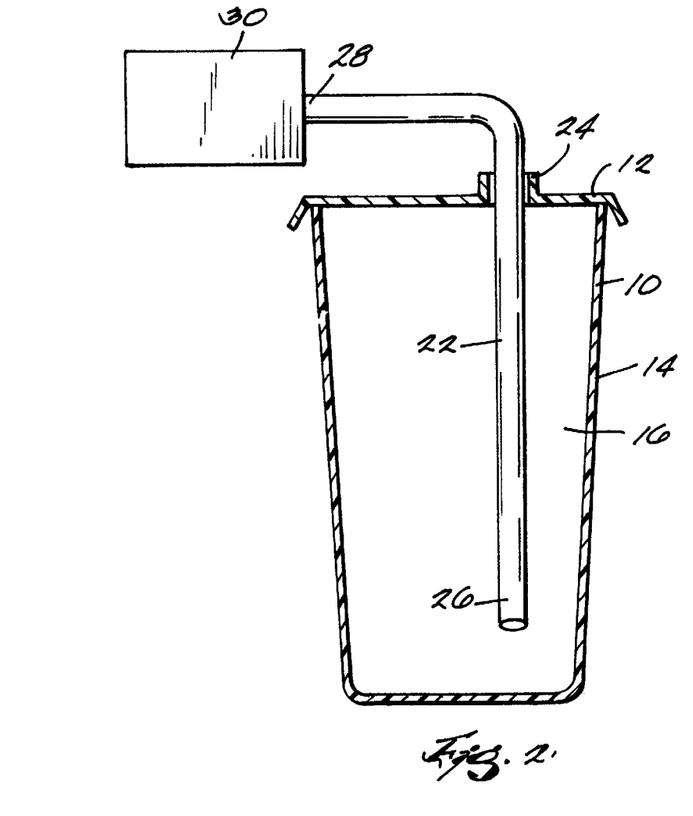
FIG. 2 is a sectional view of the apparatus and one method for draining the liner.

Turning now to FIG. 2, there is shown the liner-type medical suction apparatus 10. To drain the fluid contents of the interior 16 of the liner 14, a conduit 22 is positioned in the interior 16 of the liner 14, such as through an open port 24 in the cover 12. One end 26 of the conduit 22 is positioned in the interior 16 of the liner 14 and the other end 28 is in communication with a drainage device 30 which evacuates the fluid from the interior 16 of the liner 14. To support the apparatus during drainage, the apparatus 10 can be hung from a stand or hung from a bracket secured to a wall.

Figure 3:
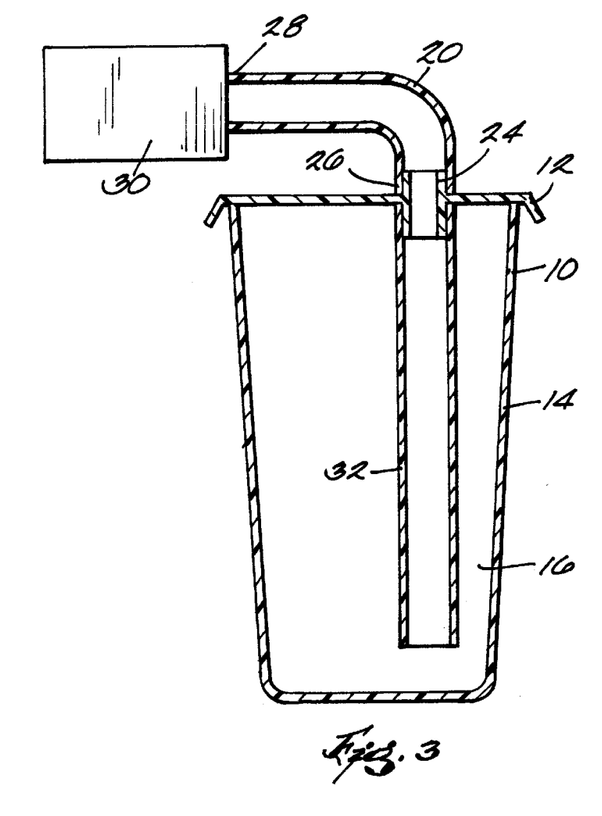
FIG. 3 is a sectional view of the apparatus and a second method for draining the liner.

With reference to FIG. 3, a second method for draining the apparatus 10 is shown. In this embodiment, a tube 32 is pre-attached to the inside of the cover 12 and hangs down into the interior 16 of the liner 14. To drain the liner 14, the end 26 of the conduit 22 is secured to the open port 24 on the cover 12 and the second end 28 is secured to the drainage device 30, such as was described above.

Figure 4:
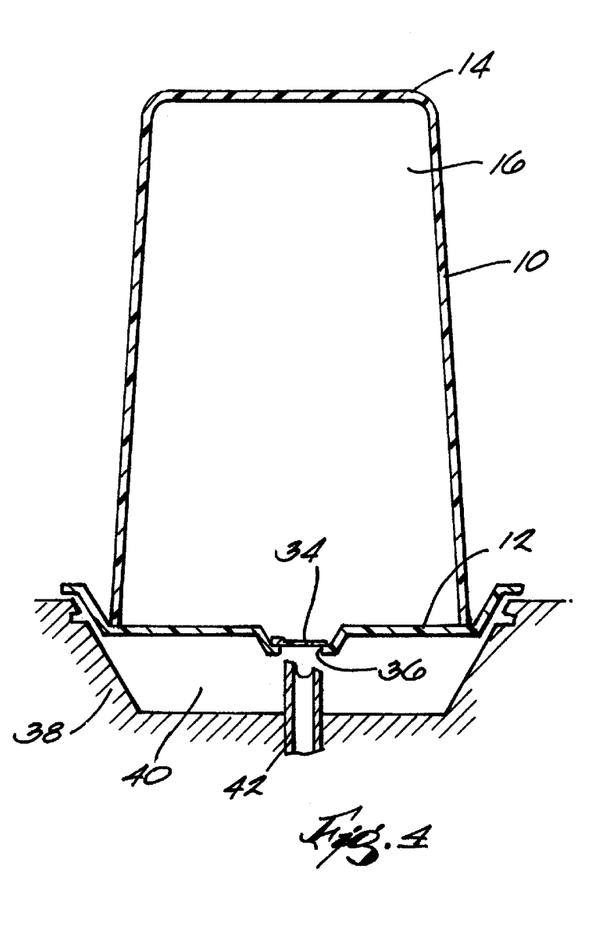
FIGS. 4 and 5 are sectional views of the apparatus and a third method for draining the liner.
Figure 5:
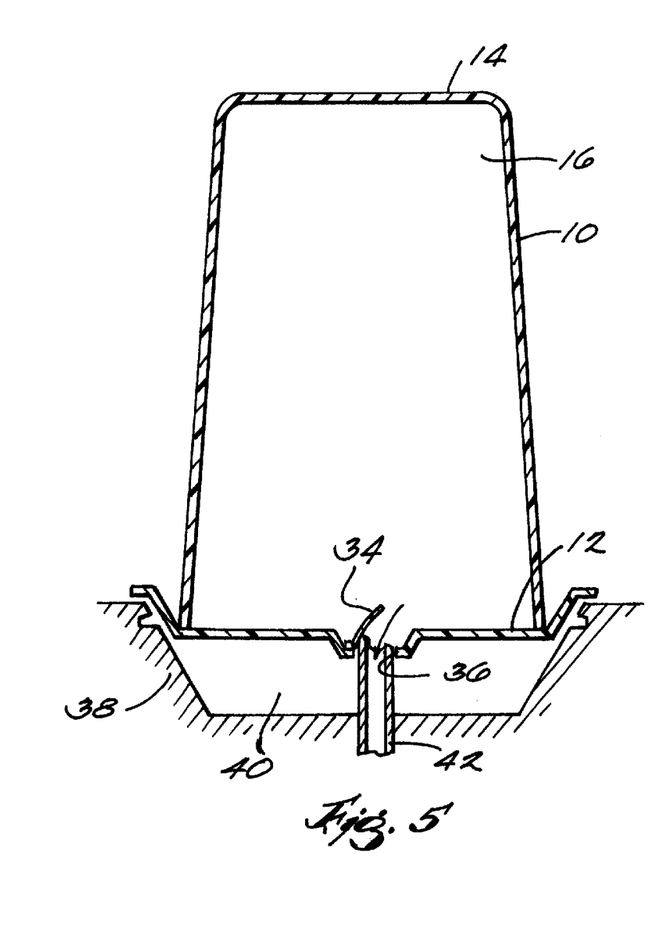

Turning now to FIGS. 4 and 5, a third method for draining the liner 14 is shown. With this method, the cover 12 includes a flapper-style valve 34 positioned in a port 36. To drain the fluid from the liner 14, the apparatus 10 is inverted with respect to a drainage device 38 and the cover 12 is positioned in a cradle 40 of the drainage device 38. Preferably, the drainage device 38 creates a negative pressure or suction force within the cradle 40 to hold the apparatus 10 in place. The drainage device 38 includes a breakout pipe 42 that is movable vertically. After the cover 12 has been positioned in the cradle 40, the pipe 42 is actuated such that it moves upwardly toward the valve 34. Further upward movement of the pipe 42 pivots the valve 34 to enable fluid to escape the liner 14 through the pipe 42 as is shown by the arrow in FIG. 5. After drainage, the pipe 42 is actuated downwardly, the valve 34 returns to its normally closed position and the apparatus 10 can be removed from the cradle 40. One suitable construction for the pipe 42 is disclosed in U.S. patent application Ser. No. 09/239,842, titled "Method and Apparatus for Removing and Disposing of Body Fluids," filed Jan. 29, 1999, the entire contents of which is incorporated herein by reference.

Figure 6:
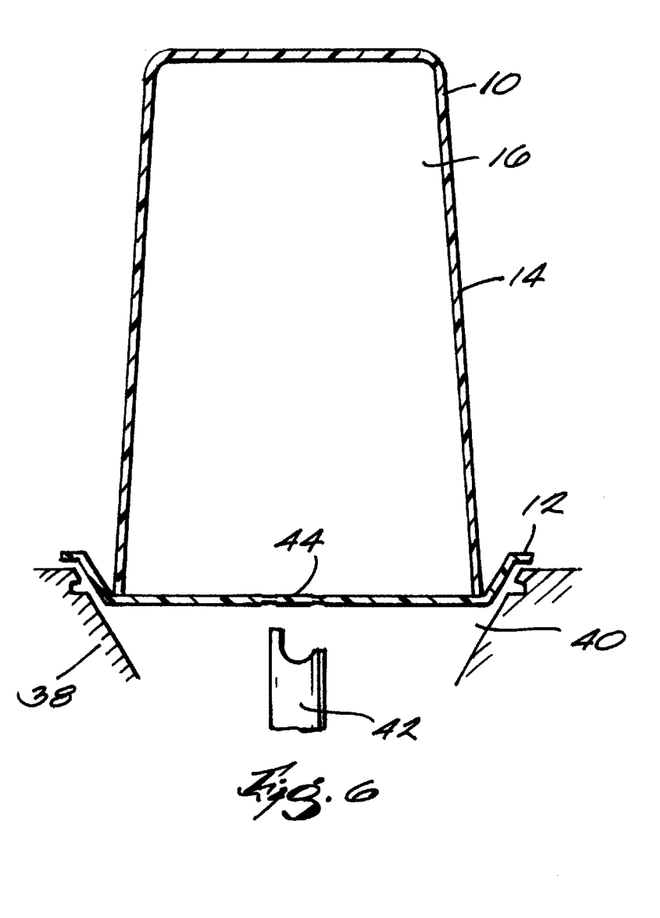
FIG. 6 is a sectional view of the apparatus and a fourth method for draining the liner.

A fourth method for draining the liner is shown in FIG. 6. In this embodiment, the cover 12 includes a breakaway portion 44. Preferably, the breakaway portion 44 is a frangible part of the cover 12. To drain the fluid from the liner 14, the apparatus 10 is inverted with respect to the drainage device 38, the cover 12 is positioned in the cradle 40, and drainage device 38 creates a suction force within the cradle 40 to hold the apparatus 10 in place. After the cover 12 has been positioned in the cradle 40, the pipe 42 is actuated upwardly toward the portion 44. Further upward movement of the pipe 42 breaks the breakaway portion 44 allowing fluid to drain from the interior 16 of the liner 14 through the pipe 42. After drainage, the pipe 42 is actuated downwardly and the apparatus 10 can be removed from the cradle 40.

Figure 7:
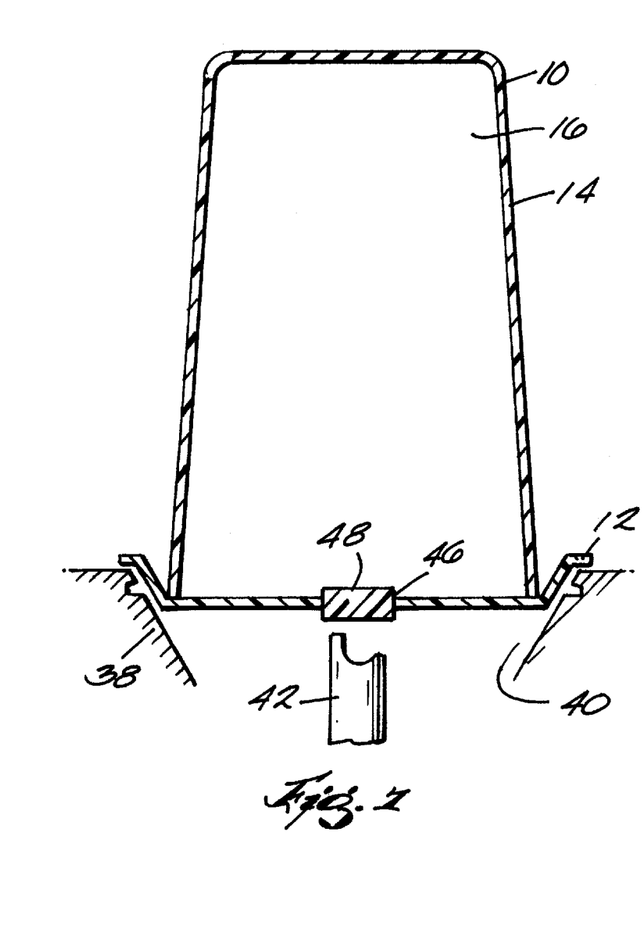
FIG. 7 is a sectional view of the apparatus and a fifth method for draining the liner.

As shown in FIG. 7, a fifth method is depicted for draining the liner 14. In this method, the cover 12 includes a port 46 that is normally occluded with a plug 48. To drain the fluid from the liner 14, the apparatus 10 is inverted with respect to the drainage device 38, the cover 12 is positioned in the cradle 40, and the drainage device 38 creates a suction force within the cradle 40 to hold the apparatus 10 in place. After the cover 12 has been positioned in the cradle 40, the pipe 42 is actuated upwardly toward the plug 48. Further upward movement of the pipe 42 dislodges the plug 48 from the port 46 allowing fluid to drain from the interior 16 of the liner 14 through the pipe 42. After drainage, the pipe 42 is actuated downwardly and the apparatus 10 can be removed from the cradle 40.

Figure 8:
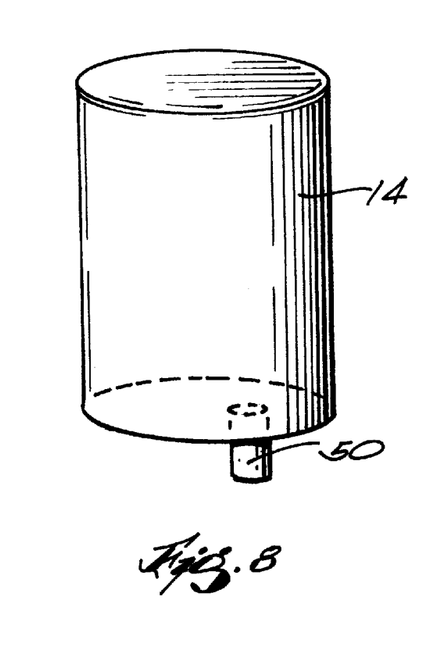
FIG. 8 is a perspective view of a liner and sixth method for draining the liner.

Turning now to FIG. 8, a sixth method is shown for draining the liner 14. In this embodiment, the liner 14 includes a nipple portion 50 on the bottom of the liner 14. To drain the contents of the liner 14, the nipple portion 50 is severed or punctured allowing fluid to drain from the interior 16 of the liner 14.

In addition to the cover structures shown in FIGS. 4–8, other cover structures may be employed. While the structures disclosed in U.S. patent application Ser. No. 09/239, 842 are generally shown as being incorporated into the bottom of a medical suction apparatus, those structures may also be incorporated into the cover of a liner-type medical suction apparatus.

Figure 9:
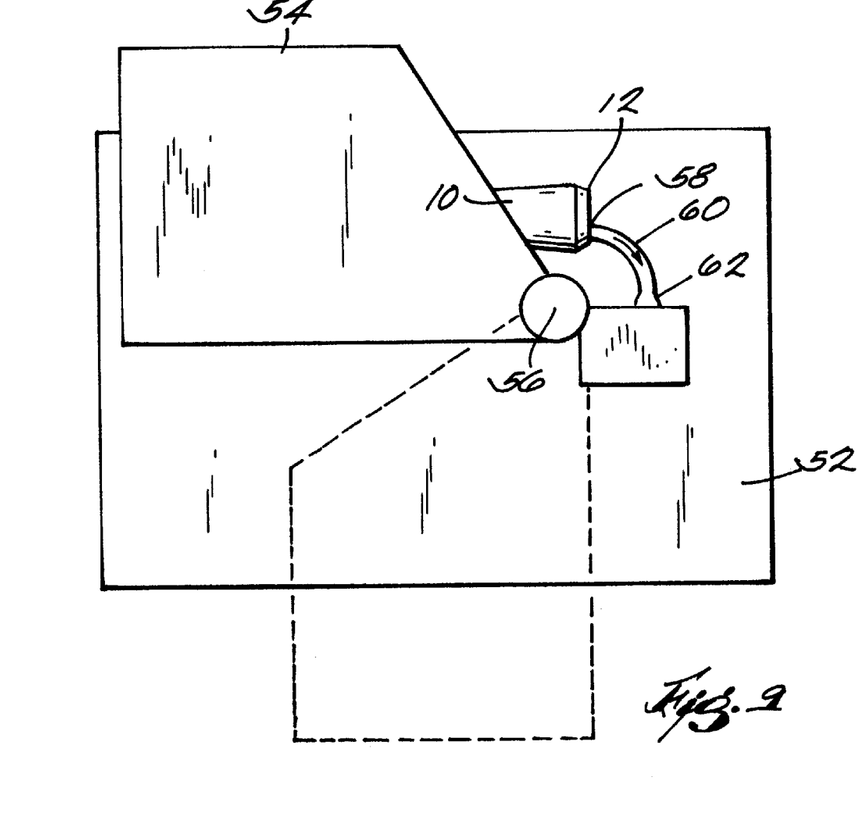
FIG. 9 is a front view of a seventh method for draining the liner.

With reference to FIG. 9, a seventh method for draining the liner 14 is shown. In this embodiment, a drainage device 52 includes a pivotable swing arm 54 that rotates about a pivot point 56. To drain the liner 14, the apparatus 10 is positioned in the swing arm 54 with the swing arm 54 in a first position, shown in phantom in FIG. 9. One end 58 of a conduit 60 is secured to a port on the cover 12 and the second end 62 of the conduit 60 is secured to the drainage device 52. The swing arm 54 is then pivoted to a second position as shown in solid lines in FIG. 9 and the contents of the liner 14 drained. The second position may be a substantially horizontal position as shown in FIG. 9, or the second position may be any position that allows as much fluid as possible to drain out of the liner 14. After drainage is completed, the swing arm 54 is returned to its first position and the apparatus 10 can be removed from the swing arm 54.

The embodiments of the drainage device shown herein can operate using various methods to drain the liner such as a venturi action, a pumping action, or the like. One example of a drainage device is the Eductor Fluid Management System available from Deknatel or Bemis Manufacturing Company. However, it should be noted that other drainage devices can be utilized and the invention herein is not limited to use of the Eductor Fluid Management System to drain the liner-type medical suction apparatuses shown herein.

Various features and advantages of the invention are set forth in the following claims.

What is claimed is:

1. A method for draining a liner-type medical suction apparatus, the liner-type medical suction apparatus including a liner, a liner interior filled with fluid, a cover, and a port in the cover, the method comprising:

providing a drainage device, the drainage device including a conduit and a cradle;

positioning the cover of the liner-type medical suction apparatus within the cradle of the drainage device with the liner-type medical suction apparatus inverted;

causing the conduit to communicate with the liner interior through the port; and draining the fluid from the liner interior through the conduit.

2. A method for draining a liner-type medical suction apparatus, the liner-type medical suction apparatus including a liner, a liner interior filled with fluid, a cover, and a port in the cover, the method comprising:

providing a drainage device, the drainage device including a conduit and a cradle;

positioning the cover of the liner-type medical suction apparatus within the cradle of the drainage device with the liner-type medical suction apparatus inverted;

causing the conduit to communicate with the liner interior through the port; and draining the fluid from the liner interior through the conduit, wherein positioning the cover of the liner-type medical suction apparatus within the cradle of the drainage device includes creating a suction force between the liner-type medical suction apparatus and the cradle.

3. A method for draining a liner-type medical suction apparatus, the liner-type medical suction apparatus including a liner, a liner interior filled with fluid, a cover, and a port in the cover, the method comprising:

providing a drainage device, the drainage device including a conduit and a cradle;

positioning the cover of the liner-type medical suction apparatus within the cradle of the drainage device with the liner-type medical suction apparatus inverted;

causing the conduit to communicate with the liner interior through the port; and draining the fluid from the liner interior through the conduit, wherein the conduit is a breakout pipe, and wherein the causing the conduit to communicate with the liner interior through the port includes causing the breakout pipe to move upwardly through the port.

4. The method of claim 3 wherein a flap valve is coupled to the port, and wherein causing the breakout pipe to move upwardly through the port includes causing the breakout pipe to move the flap valve from a closed position to an open position.

5. The method of claim 3 wherein the port is covered by a frangible portion, and wherein causing the breakout pipe to move upwardly through the port includes causing the breakout pipe to break the frangible portion.

6. The method of claim 3 wherein the port is occluded with a plug, and wherein causing the breakout pipe to move upwardly through the port includes causing the breakout pipe to dislodge the plug.

7. The method of claim 3 wherein the port is occluded by a nipple, and wherein causing the breakout pipe to move upwardly through the port includes causing the breakout pipe to puncture the nipple.

8. A method for draining a liner-type medical suction apparatus, the liner-type medical suction apparatus including a liner, a liner interior filled with fluid, a cover, and a port in the cover, the method comprising:

providing a drainage device, the drainage device including a movable support member and a conduit;

positioning the liner-type medical suction apparatus in a substantially upright position within the support member;

attaching the conduit to the port; and moving the support member to cause the liner-type medical suction apparatus to move from the substantially upright position to a position in which the fluid flows out of the liner interior into the conduit.

9. The method of claim 8 wherein the support member is a pivotable swing arm, and wherein causing the liner-type medical suction apparatus to move from the substantially upright position to a position in which the fluid flows out of the liner interior into the conduit includes rotating the pivotable swing arm from the substantially upright position to a position in which the fluid flows out of the liner interior into the conduit.

10. Medical apparatus comprising:

a liner-type medical suction apparatus including a liner, a liner interior for containing fluid, a cover, a first port in the cover, a pre-attached tube coupled to the first port and extending into the liner interior, and a second port in the cover;

a drainage device including a housing and a support member adapted to support the liner-type medical suction apparatus; and a conduit including a first end coupled to the drainage device housing and a second end coupleable to the second port so that fluid in the liner interior can flow through the pre-attached tube and out of the second port to the drainage device.

11. The device of claim 10 wherein the cover of the liner-type medical suction apparatus includes a first boss extending upwardly from the second port and a second boss extending downwardly from the first port, and wherein the conduit is coupleable to the first boss and the pre-attached tube is coupled to the second boss.

12. A device for draining a liner-type medical suction apparatus, the liner-type medical suction apparatus including a liner, a liner interior filled with fluid, and a cover, the device comprising:

a drainage device housing;

a cradle in the drainage device housing, the cradle being adapted to support the cover of the liner-type medical suction apparatus when the liner-type medical suction apparatus is in an inverted position; and a breakout pipe including a first end coupled to the cradle and a second end for communication with the liner interior, the breakout pipe being movable upwardly between a storage position in which the second end is stored substantially within the cradle and a drainage position in which the second end is in communication with the liner interior through the cover.

13. A device for draining a liner-type medical suction apparatus, the liner-type medical suction apparatus including a liner, a liner interior filled with fluid, and a cover, the device comprising:

a drainage device housing;

a cradle coupled to the drainage device housing, the cradle being adapted to support the cover of the liner-type medical suction apparatus when the liner-type medical suction apparatus is in an inverted position; and a breakout pipe including a first end coupled to the cradle and a second end for communication with the liner interior, the breakout pipe being movable upwardly between a storage position in which the second end is stored substantially within the cradle and a drainage position in which the second end is in communication with the liner interior through the cover, wherein the cradle is adapted to create a suction force between the cradle and the cover of the liner-type medical suction apparatus.

14. The device of claim 12 wherein the cover includes a flap valve, and wherein the breakout pipe moves the flap valve between a closed position when the breakout pipe is in the storage position and an open position when the breakout pipe is in the drainage position.

15. The device of claim 12 wherein the cover includes a frangible portion, and wherein the breakout pipe is adapted to break the frangible portion when the breakout pipe is moved upwardly into the drainage position.

16. The device of claim 12 wherein the cover includes a port occluded by a plug, and wherein the breakout pipe is adapted to dislodge the plug when the breakout pipe is moved upwardly into the drainage position.

17. The device of claim 12 wherein the cover includes a port occluded by a nipple, and wherein the breakout pipe is adapted to create a fluid passage through the nipple when the breakout pipe is moved upwardly into the drainage position.

18. The device of claim 17 wherein the breakout pipe is adapted to create a fluid passage through the nipple by puncturing the nipple.

19. A device for draining a liner-type medical suction apparatus, the liner-type medical suction apparatus including a liner, a liner interior, a cover, and a port in the cover, the device comprising:

a drainage device housing;

a drain coupled to the drainage device housing;

a conduit including a first end coupled to the drain and a second end adapted for attachment to the port; and a support member coupled to the drainage device housing and adapted to support the liner-type medical suction apparatus, the support member being movable between a loading position in which the liner-type medical suction apparatus is in a substantially upright position and a drainage position in which the liner-type medical suction apparatus is in a position in which the fluid flows through the conduit to the drain.

20. The device of claim 19 wherein the support member is a pivotable swing arm rotatably coupled to the drainage device housing, the pivotable swing arm being rotatable between a loading position in which the liner-type medical suction apparatus is in a substantially upright position and a drainage position in which the liner-type medical suction apparatus is in a position in which the fluid flows through the conduit to the drain.

21. A method for draining a liner-type medical suction apparatus, the liner-type medical suction apparatus including a liner, a liner interior filled with fluid, a cover, and a port in the cover, the method comprising:

providing a drainage device including a support member and a conduit;

positioning the liner-type medical suction apparatus in a first position with respect to the support member;

attaching the conduit to the port; and moving the support member to cause the liner-type medical suction apparatus to move from the first position to a second position in which the fluid flows out of the liner interior into the conduit.

22. The method of claim 21 wherein the support member is a pivotable swing arm, and wherein causing the liner-type medical suction apparatus to move from the first position to a second position includes rotating the pivotable swing arm from a substantially upright position to a position in which the fluid flows out of the liner interior into the conduit.

23. A device for draining a liner-type medical suction apparatus, the liner-type medical suction apparatus including a liner, a liner interior, a cover, and a port in the cover, the device comprising:

a drainage device housing;

a drain coupled to the drainage device housing;

a conduit including a first end coupled to the drain and a second end adapted for attachment to the port; and a support member coupled to the drainage device housing, the support member being movable between a first position and a second position in which the liner-type medical suction apparatus is in a position in which the fluid flows through the conduit to the drain, wherein the support member is a pivotable swing arm rotatably coupled to the drainage device housing, the pivotable swing arm being rotatable between a loading position in which the liner-type medical suction apparatus is in a substantially upright position and a drainage position in which the liner-type medical suction apparatus is in a position in which the fluid flows through the conduit to the drain.

* * * * *